(12) United States Patent
Schaus et al.

(10) Patent No.: US 6,608,079 B1
(45) Date of Patent: Aug. 19, 2003

(54) INDOLE DERIVATIVES AND THEIR USE AS 5-HT$_1$F AGONISTS

(75) Inventors: John Mehnert Schaus, Zionsville, IN (US); Yao-Chang Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/857,571
(22) PCT Filed: Dec. 9, 1999
(86) PCT No.: PCT/US99/29224
§ 371 (c)(1), (2), (4) Date: Jun. 5, 2001
(87) PCT Pub. No.: WO00/34266
PCT Pub. Date: Jun. 15, 2000

Related U.S. Application Data
(60) Provisional application No. 60/111,869, filed on Dec. 11, 1998.

(51) Int. Cl.$^7$ ............... A61K 31/437; A61K 31/4439; A61K 31/404; C07D 401/04; C07D 403/04; A61P 25/06
(52) U.S. Cl. ............... 514/299; 514/323; 514/339; 514/306; 514/214.01; 514/414; 540/593; 546/201; 546/277.4; 546/138; 546/112; 548/468
(58) Field of Search ............... 546/201, 277.4, 546/138, 112; 540/593; 548/468; 514/299, 323, 339, 306, 214.01, 414

(56) References Cited

U.S. PATENT DOCUMENTS 5,708,008 A 1/1998 Audia et al.
5,817,671 A 10/1998 Filla et al.
5,874,427 A * 2/1999 Filla .......................... 514/214

FOREIGN PATENT DOCUMENTS

| EP | 0 708 102 A1 | 4/1996 |
| EP | 0 714 894 A1 | 6/1996 |
| EP | 0 842 934 A1 | 5/1998 |
| EP | 0 882 726 A1 | 12/1998 |
| WO | WO 98 15545 | 4/1998 |
| WO | WO 98 46570 | 10/1998 |

OTHER PUBLICATIONS

King FD. Medicinal Chemistry: Principles and Practice. The Royal Society of Chemistry. pp. 206–208. (1994).*

* cited by examiner

Primary Examiner—Evelyn Mei Huang
(74) Attorney, Agent, or Firm—R. Craig Tucker

(57) ABSTRACT

The present invention relates to a compound of formula (I), or a pharmaceutical acid addition salt thereof, which are useful for activating 5-HT$_{1F}$ receptors and inhibiting neuronal protein extravasation in a mammal.

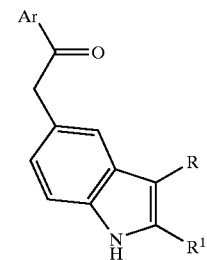

(I)

24 Claims, No Drawings

INDOLE DERIVATIVES AND THEIR USE AS 5-HT$_1$F AGONISTS

This U.S. national stage application of International Application PCT/US99/29224, filed Dec. 9, 1999, claims priority to U.S. provisional application Serial No. 60/111,869, filed Dec. 11, 1998.

Theories regarding the pathophysiology of migraine have been dominated since 1938 by the work of Graham and Wolff. *Arch. Neurol. Psychiatry*, 39:737–63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. Humphrey, et al., *Ann. NY Acad. Sci.*, 600:587–600, 1990. Recent work by Moskowitz has shown, however, that the occurrence of migraine headaches is independent of changes in vessel diameter. *Cephalalgia*, 12:5–7, 1992.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16–S20 1993.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408–412, 1993. This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention relates to novel 5-HT$_{1F}$ agonists which inhibit peptide extravasation due to stimulation of the trigeminal ganglia, and are therefore useful for the treatment of migraine and associated disorders.

The present invention relates to a compound of formula I:

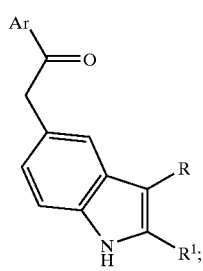

or a pharmaceutical acid addition salt thereof, where;

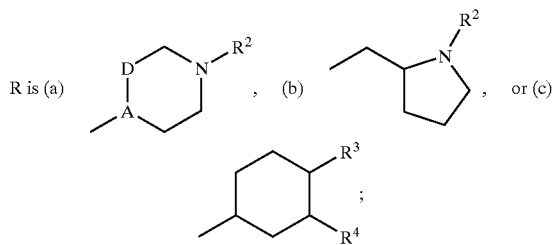

A—D is CH—CH$_2$ or C=CH;
R$^1$ is hydrogen or C$_1$–C$_4$ alkyl;
R$^2$ is hydrogen, C$_1$–C$_6$ alkyl, C$_2$–C$_6$ alkenyl, C$_2$–C$_6$ alkynyl, Ar, or Ar—(C$_1$–C$_4$ alkyl);
R$^3$ and R$^4$ combine, together with the 6 membered ring to which they are attached, to form a 6:5, 6:6, or 6:7 fused bicyclic ring; and
Ar is an optionally substituted phenyl or optionally substituted heteroaryl.

This invention also relates to a pharmaceutical formulation comprising a compound of formula I, or a pharmaceutical acid addition salt thereof, and a pharmaceutical carrier, diluent, or excipient.

In addition, the present invention relates to a method for activating 5-HT$_{1F}$ receptors in mammals comprising administering to a mammal in need of such activation an effective amount of a compound of formula I, or a pharmaceutical acid addition salt thereof.

Moreover, the current invention relates to a method for inhibiting neuronal protein extravasation comprising administering to a mammal in need of such inhibition an effective amount of a compound of formula I, or a pharmaceutical acid addition salt thereof.

One embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, chronic pain, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of formula I.

The use of a compound of formula I for the activation of the 5-HT$_{1F}$ receptor, for the inhibition of peptide extravasation in general or due to stimulation of the trigeminal ganglia specifically, and for the treatment of any of the disorders described above, are all embodiments of the present invention.

The general chemical terms used throughout have their usual meanings. For example, the term "C$_1$–C$_4$ alkyl" refers to methyl, ethyl, n-propyl, isopropyl, cyclopropyl, n-butyl, isobutyl, sec-butyl, tert-butyl and cyclobutyl. The term "$C_1$–$C_6$ alkyl" includes those groups listed for $C_1$–$C_4$ alkyl and also refers to saturated, straight, branched, or cyclic hydrocarbon chains of 5 to 6 carbon atoms. Such groups include pentyl, pent-2-yl, pent-3-yl, neopentyl, hexyl, and the like. The term "$C_3$–$C_8$ cycloalkyl" refers to cyclopropyl, cyclobutyl, cyclopentyl, cyclohexyl, cycloheptyl, and cyclooctyl.

The term "$C_2$–$C_6$ alkenyl" refers to mono-unsaturated straight or branched hydrocarbon chains containing from 2 to 6 carbon atoms and includes vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like.

The term "$C_2$–$C_6$ alkynyl" refers to straight or branched hydrocarbon chains containing 1 triple bond and from 2 to 6 carbon atoms and includes acetylenyl, propynyl, 2-butyn-4-yl, 1-butyn-4-yl, 1-pentyn-5-yl, 2-pentyn-5-yl and the like.

The terms "$C_1$–$C_6$ alkoxy" and "$C_1$–$C_4$ alkoxy" refer respectively to a $C_1$–$C_6$ alkyl and $C_1$–$C_4$ alkyl group bonded through an oxygen atom. The term "$C_1$–$C_4$ acyl" refers to a formyl group or a $C_1$–$C_3$ alkyl group bonded through a carbonyl moiety.

The term "halo" includes fluoro, chloro, bromo and iodo.

The term "heteroaryl" is taken to mean an aromatic 5- or 6-membered ring containing from 1 to 3 heteroatoms selected from: nitrogen, oxygen, and sulfur. Examples include furanyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like.

The term "substituted heteroaryl" is taken to mean that the heteroaryl moiety is substituted with substituents selected from the group consisting of halo, nitro, cyano, amino, trifluoromethyl, trifluoromethoxy, phenyl, benzoyl, $C_1$–$C_6$ alkyl, $C_1$–$C_6$ alkoxy, $C_1$–$C_4$ acyl, and $(C_1$–$C_4)_n$ amino where n is 0, 1, or 2.

The terms "substituted phenyl" and "substituted phenyl ($C_1$–$C_4$ alkyl)" are taken to mean that the phenyl moiety in either case is substituted with one substituent selected from the group consisting of halo, nitro, cyano, amino, trifluoromethyl, trifluoromethoxy, phenyl, benzoyl, $C_1$–$C_6$ alkyl, $C_1$–$C_6$ alkoxy, $(C_1$–$C_4$ alkyl)$S(O)_n$ where n is 0, 1, or 2, $(C_1$–$C_4$ alkyl)$_2$ amino, $C_1$–$C_4$ acyl, or two to three substituents independently selected from the group consisting of halo, nitro, trifluoromethyl, $C_1$–$C_4$ alkyl, or $C_1$–$C_4$ alkoxy.

The term "amino protecting group" as used in this specification refers to substituents commonly employed to block or protect the amino functionality while reacting to other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as "Greene".

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

Since the compounds of this invention are amines, they are basic in nature and accordingly react with any of a number of inorganic and organic acids to form pharmaceutical acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

The term "effective amount" means an amount of a compound of formula I which is capable of activating 5-$HT_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

All enantiomers, diastereomers, and mixtures thereof, are included within the scope of the present invention. The compounds of formula I where $R^1$ and $R^2$ combine, together with the 6 membered ring to which they are attached, to form a 6:5, 6:6, or 6:7 fused bicyclic ring (indolizinyl, quinolizinyl, or 1-azabicyclo[5.4.0]undecanyl ring respectively) contain a chiral center located in that bicyclic ring. This chiral center is located at the bridgehead carbon in the ring system. Such centers are designed "R" or "S." For the purposes of the present application, the numbering system for naming the substituents around the indole ring and the R and S enantiomers are illustrated below where $R^1$ and Ar are as defined above.

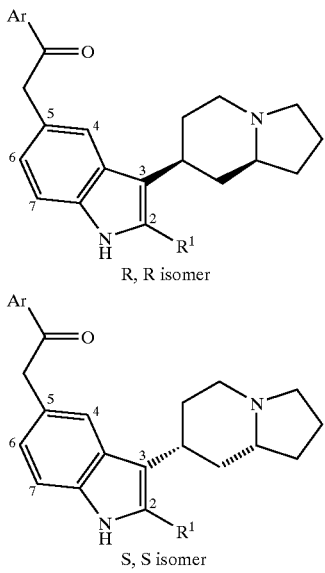

The following group is illustrative of compounds contemplated within the scope of this invention:

- 5-(2-fluorobenzoylmethyl)-3-(1-methyl-1,2,3,6-tetrahydropyrid-4-yl)indole
- 5-(3-fluorobenzoylmethyl)-3-(1-methyl-1,2,3,6-tetrahydropyrid-4-yl)indole
- 5-(2,3-difluorobenzoylmethyl)-3-(1-methyl-1,2,3,6-tetrahydropyrid-4-yl)indole methanesulfonate
- 5-(2,5-difluorobenzoylmethyl)-3-(1-methyl-1,2,3,6-tetrahydropyrid-4-yl)indole acetate
- 5-(2,6-difluorobenzoylmethyl)-3-(1-methyl-1,2,3,6-tetrahydropyrid-4-yl)indole
- 5-(2,3,4-trifluorobenzoylmethyl)-3-(1-methyl-1,2,3,6-tetrahydropyrid-4-yl)indole
- 5-(2,3,5-trifluorobenzoylmethyl)-3-(1-methyl-1,2,3,6-tetrahydropyrid-4-yl)indole carbonate
- 5-(2,3,6-trifluorobenzoylmethyl)-3-(1-methyl-1,2,3,6-tetrahydropyrid-4-yl)indole
- 5-(2-chlorobenzoylmethyl)-3-(1-methyl-1,2,3,6-tetrahydropyrid-4-yl)indole
- 5-(3-chlorobenzoylmethyl)-3-(1-methyl-1,2,3,6-tetrahydropyrid-4-yl)indole
- 5-(2,4-dichlorobenzoylmethyl)-3-(1-methyl-1,2,3,6-tetrahydropyrid-4-yl)indole
- 5-(2,3,5-trichlorobenzoylmethyl)-3-(1-methyl-1,2,3,6-tetrahydropyrid-4-yl)indole p-toluenesulfonate
- 5-(3-bromobenzoylmethyl)-3-(1-methyl-1,2,3,6-tetrahydropyrid-4-yl)indole
- 5-(2,3-dibromobenzoylmethyl)-3-(1-methyl-1,2,3,6-tetrahydropyrid-4-yl)indole oxalate
- 5-(2,3-diiodobenzoylmethyl)-3-(1-methyl-1,2,3,6-tetrahydropyrid-4-yl)indole
- 5-(4-nitrobenzoylmethyl)-3-(1-methyl-1,2,3,6-tetrahydropyrid-4-yl)indole
- 5-(3-nitrobenzoylmethyl)-3-(1-methyl-1,2,3,6-tetrahydropyrid-4-yl)indole
- 5-(3-aminobenzoylmethyl)-3-(1-methyl-1,2,3,6-tetrahydropyrid-4-yl)indole
- 5-(2,4-dimethylbenzoylmethyl)-3-(1-methyl-1,2,3,6-tetrahydropyrid-4-yl)indole
- 5-(3-isopropylbenzoylmethyl)-3-(1-methyl-1,2,3,6-tetrahydropyrid-4-yl)indole
- 5-(3-methoxybenzoylmethyl)-3-(1-methyl-1,2,3,6-tetrahydropyrid-4-yl)indole
- 5-(2-methylaminobenzoylmethyl)-3-(1-methyl-1,2,3,6-tetrahydropyrid-4-yl)indole
- 5-(3-trifluoromethoxybenzoylmethyl)-3-(1-methyl-1,2,3,6-tetrahydropyrid-4-yl)indole
- 5-(2-cyanobenzoylmethyl)-3-(1-methyl-1,2,3,6-tetrahydropyrid-4-yl)indole
- 5-(3-phenylbenzoylmethyl)-3-(1-methyl-1,2,3,6-tetrahydropyrid-4-yl)indole
- 5-(2-fluoro-3-chlorobenzoylmethyl)-3-(1-methyl-1,2,3,6-tetrahydropyrid-4-yl)indole
- 5-(3-chlorobenzoylmethyl)-3-(1-methylpiperidin-4-yl)indole
- 5-(2,3-dichlorobenzoylmethyl)-3-(1-methylpiperidin-4-yl)indole
- 5-(2,4-dichlorobenzoylmethyl)-3-(1-methylpiperidin-4-yl)indole
- 5-(2,3,5-trichlorobenzoylmethyl)-3-(1-methylpiperidin-4-yl)indole
- 5-(2-bromobenzoylmethyl)-3-(1-methylpiperidin-4-yl)indole
- 5-(3-iodobenzoylmethyl)-3-(1-methylpiperidin-4-yl)indole
- 5-(3-methylbenzoylmethyl)-3-(1-methylpiperidin-4-yl)indole
- 5-(2,3-dimethylbenzoylmethyl)-3-(1-methylpiperidin-4-yl)indole
- 5-(2,4-dimethylbenzoylmethyl)-3-(1-methylpiperidin-4-yl)indole
- 5-(2,5-dimethylbenzoylmethyl)-3-(1-methylpiperidin-4-yl)indole
- 5-(2,6-dimethylbenzoylmethyl)-3-(1-methylpiperidin-4-yl)indole
- 5-(3-ethylbenzoylmethyl)-3-(1-methylpiperidin-4-yl)indole
- 5-(2-isopropylbenzoylmethyl)-3-(1-methylpiperidin-4-yl)indole
- 5-(3-isopropylbenzoylmethyl)-3-(1-methylpiperidin-4-yl)indole
- 5-(2,3-diisopropylbenzoylmethyl)-3-(1-methylpiperidin-4-yl)indole
- 5-(2,4-diisopropylbenzoylmethyl)-3-(1-methylpiperidin-4-yl)indole
- 5-(2-butylbenzoylmethyl)-3-(1-methylpiperidin-4-yl)indole
- 5-(3-butylbenzoylmethyl)-3-(1-methylpiperidin-4-yl)indole
- 5-(2,3-dibutylbenzoylmethyl)-3-(1-methylpiperidin-4-yl)indole
- 5-(2,3,4-tributylbenzoylmethyl)-3-(1-methylpiperidin-4-yl)indole
- 5-(3-pentylbenzoylmethyl)-3-(1-methylpiperidin-4-yl)indole
- 5-(2-isobutylbenzoylmethyl)-3-(1-methylpiperidin-4-yl)indole 5-3-isobutylbenzoylmethyl)-3-(1-methylpiperidin-4-yl)indole
5-(2-methoxybenzoylmethyl)-3-(1-methylpiperidin-4-yl)indole
5-(3-methylaminobenzoylmethyl)-3-(1-methylpiperidin-4-yl)indole
5-(2,3-dimethylaminobenzoylmethyl)-3-(1-methylpiperidin-4-yl)indole
5-(2,5-dimethylaminobenzoylmethyl)-3-(1-methylpiperidin-4-yl)indole
5-(3-fluorobenzoylmethyl)-3-[(1-methylpyrrolidin-2-yl)methyl]indole
5-(2,3-difluorobenzoylmethyl)-3-[(1-methylpyrrolidin-2-yl)methyl]indole
5-(2,4-difluorobenzoylmethyl)-3-[(1-methylpyrrolidin-2-yl)methyl]indole
5-(2,5-difluorobenzoylmethyl)-3-[(1-methylpyrrolidin-2-yl)methyl]indole
5-(3,4-difluorobenzoylmethyl)-3-[(1-methylpyrrolidin-2-yl)methyl]indole
5-(3-chlorobenzoylmethyl)-3-[(1-methylpyrrolidin-2-yl)methyl]indole
5-(2,3-dichlorobenzoylmethyl)-3-[(1-methylpyrrolidin-2-yl)methyl]indole
5-(2,4-dichlorobenzoylmethyl)-3-[(1-methylpyrrolidin-2-yl)methyl]indole
5-(3,5-dichlorobenzoylmethyl)-3-[(1-methylpyrrolidin-2-yl)methyl]indole
5-(2,5-dibromobenzoylmethyl)-3-[(1-methylpyrrolidin-2-yl)methyl]indole
5-(2,6-dibromobenzoylmethyl)-3-[(1-methylpyrrolidin-2-yl)methyl]indole
5-(3-iodobenzoylmethyl)-3-[(1-methylpyrrolidin-2-yl)methyl]indole
5-(2,3-diiodobenzoylmethyl)-3-[(1-methylpyrrolidin-2-yl)methyl]indole
5-(2-nitrobenzoylmethyl)-3-[(1-methylpyrrolidin-2-yl)methyl]indole
5-(3-nitrobenzoylmethyl)-3-[(1-methylpyrrolidin-2-yl)methyl]indole
5-(2,3,4-trinitrobenzoylmethyl)-3-[(1-methylpyrrolidin-2-yl)methyl]indole
5-(4-aminobenzoylmethyl)-3-[(1-methylpyrrolidin-2-yl)methyl]indole
5-(3-aminobenzoylmethyl)-3-[(1-methylpyrrolidin-2-yl)methyl]indole
5-(2,3-diaminobenzoylmethyl)-3-[(1-methylpyrrolidin-2-yl)methyl]indole
5-(2,4-diaminobenzoylmethyl)-3-[(1-methylpyrrolidin-2-yl)methyl]indole
5-(3-methylbenzoylmethyl)-3-[(1-methylpyrrolidin-2-yl)methyl]indole
5-(3-isopropylbenzoylmethyl)-3-[(1-methylpyrrolidin-2-yl)methyl]indole
5-(2,3-diisopropylbenzoylmethyl)-3-[(1-methylpyrrolidin-2-yl)methyl]indole
5-(2-isobutylbenzoylmethyl)-3-[(1-methylpyrrolidin-2-yl)methyl]indole
5-(3-isobutylbenzoylmethyl)-3-[(1-methylpyrrolidin-2-yl)methyl]indole
5-(2,3-diisobutylbenzoylmethyl)-3-[(1-methylpyrrolidin-2-yl)methyl]indole
5-(3,4-diisobutylbenzoylmethyl)-3-[(1-methylpyrrolidin-2-yl)methyl]indole
5-(3,5-diisobutylbenzoylmethyl)-3-[(1-methylpyrrolidin-2-yl)methyl]indole
5-(2-methoxybenzoylmethyl)-3-[(1-methylpyrrolidin-2-yl)methyl]indole
5-(3-methoxybenzoylmethyl)-3-[(1-methylpyrrolidin-2-yl)methyl]indole
5-(2,4-dimethoxybenzoylmethyl)-3-[(1-methylpyrrolidin-2-yl)methyl]indole
5-(2,6-dimethoxybenzoylmethyl)-3-[(1-methylpyrrolidin-2-yl)methyl]indole
5-(2-ethoxybenzoylmethyl)-3-[(1-methylpyrrolidin-2-yl)methyl]indole
5-(2-methylaminobenzoylmethyl)-3-[(1-methylpyrrolidin-2-yl)methyl]indole
5-(3-methylaminobenzoylmethyl)-3-[(1-methylpyrrolidin-2-yl)methyl]indole
5-(2,3-dimethylaminobenzoylmethyl)-3-[(1-methylpyrrolidin-2-yl)methyl]indole
5-(3-ethylaminobenzoylmethyl)-3-[(1-methylpyrrolidin-2-yl)methyl]indole
5-(2-fluorobenzoylmethyl)-3-(indolizidin-6-yl)indole
5-(3-fluorobenzoylmethyl)-3-(indolizidin-6-yl)indole
5-(2,3-difluorobenzoylmethyl)-3-(indolizidin-6-yl)indole
5-(2,4-difluorobenzoylmethyl)-3-(indolizidin-6-yl)indole
5-(2,5-difluorobenzoylmethyl)-3-(indolizidin-6-yl)indole
5-(2,6-difluorobenzoylmethyl)-3-(indolizidin-6-yl)indole
5-(2,4,5-trifluorobenzoylmethyl)-3-(indolizidin-6-yl)indole
5-(3,5-difluorobenzoylmethyl)-3-(indolizidin-6-yl)indole
5-(2-chlorobenzoylmethyl)-3-(indolizidin-6-yl)indole
5-(3-chlorobenzoylmethyl)-3-(indolizidin-6-yl)indole
5-(2,3-dichlorobenzoylmethyl)-3-(indolizidin-6-yl)indole
5-(2-bromobenzoylmethyl)-3-(indolizidin-6-yl)indole
5-(3-bromobenzoylmethyl)-3-(indolizidin-6-yl)indole
5-(2,4-dibromobenzoylmethyl)-3-(indolizidin-6-yl)indole
5-(2,6-dibromobenzoylmethyl)-3-(indolizidin-6-yl)indole
5-(2-iodobenzoylmethyl)-3-(indolizidin-6-yl)indole
5-(3-iodobenzoylmethyl)-3-(indolizidin-6-yl)indole
5-(2-nitrobenzoylmethyl)-3-(indolizidin-6-yl)indole
5-(3-nitrobenzoylmethyl)-3-(indolizidin-6-yl)indole
5-(2-aminobenzoylmethyl)-3-(indolizidin-6-yl)indole
5-(3-aminobenzoylmethyl)-3-(indolizidin-6-yl)indole
5-(2-methylbenzoylmethyl)-3-(indolizidin-6-yl)indole
5-(3-methylbenzoylmethyl)-3-(indolizidin-6-yl)indole
5-(2,4-dimethylbenzoylmethyl)-3-(indolizidin-6-yl)indole
5-(2-isopropylbenzoylmethyl)-3-(indolizidin-6-yl)indole
5-(3-isopropylbenzoylmethyl)-3-(indolizidin-6-yl)indole
5-(2-methoxybenzoylmethyl)-3-(indolizidin-6-yl)indole
5-(3-methoxybenzoylmethyl)-3-(indolizidin-6-yl)indole
5-(2-methylaminobenzoylmethyl)-3-(indolizidin-6-yl)indole
5-(3-methylaminobenzoylmethyl)-3-(indolizidin-6-yl)indole
5-(2-thien-3-ylethylcarbonyl)-3-(1-methylpiperidin-4-yl)indole 5-(2-pyridin-4-ylethylcarbonyl)-3-(1-methylpiperidin-4-yl)indole 5-(2-furan-3-ylethylcarbonyl)-3-(1-methylpiperidin-4-yl)indole 5-(2-pyrrol-1-ylethylcarbonyl)-3-(1-methylpiperidin-4-yl)indole 5-(2-N-methylpyrrol-2-ylethylcarbonyl)-3-(1-methylpiperidin-4-yl)indole 5-(2-oxazol-2-ylethylcarbonyl)-3-(1-methylpiperidin-4-yl)indole 5-(2-isoxazol-4-ylethylcarbonyl)-3-(1-methylpiperidin-4-yl)indole 5-(2-pyrazol-4-ylethylcarbonyl)-3-(1-methylpiperidin-4-yl)indole 5-(2-imidazol-2-ylethylcarbonyl)-3-(1-methylpiperidin-4-yl)indole 5-(2-1,2,4-triazol-5-ylethylcarbonyl)-3-(1-methylpiperidin-4-yl)indole 5-(2-1,3,4-oxadiazol-2-ylethylcarbonyl)-3-(1-methylpiperidin-4-yl)indole 5-(2-1,3,4-thiadiazol-2-ylethylcarbonyl)-3-(1-methylpiperidin-4-yl)indole 5-(2-pyrimidin-5-ylethylcarbonyl)-3-(1-methylpiperidin-4-yl)indole 5-(2-pyrazin-1-ylethylcarbonyl)-3-(1-methylpiperidin-4-yl)indole 5-(2-pyridazin-4-ylethylcarbonyl)-3-(1-methylpiperidin-4-yl)indole While all enantiomers, diastereomers, and mixtures thereof, are useful as 5-$HT_{1F}$ agonists, single enantiomers and single diastereomers are preferred. Furthermore, while all of the compounds of this invention are useful as 5-$HT_{1F}$ agonists, certain classes are preferred. The following paragraphs describe such preferred classes.

1) A—D is CH—$CH_2$;
2) A—D is C=CH;
3) R is piperidin-4-yl;
4) R is 1-methylpiperidin-4-yl;
5) R is 1,2,3,6-tetrahydropiperidin-4-yl;
6) R is 1-methyl-1,2,3,6-tetrahydropiperidin-4-yl;
7) R is indolizidin-6-yl;
8) R is [pyrrolidin-2-yl]methyl;
9) $R^1$ is hydrogen;
10) $R^1$ is methyl;
11) Ar is phenyl;
12) Ar is substituted phenyl;
13) Ar is 4-fluorophenyl;
14) Ar is heteroaryl;
15) Ar is selected from the group consisting of furanyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, and pyridazinyl;
16) Ar is substituted heteroaryl;
17) $R^2$ is hydrogen;
18) $R^2$ is methyl;
19) the compound is an acid addition salt;
20) the compound is the hydrochloride salt;
21) the compound is the oxalate salt; and
22) the compound is the fumarate salt.

It will be understood that the above classes may be combined to form additional preferred classes.

It is preferred that the mammal to be treated by the administration of compounds of this invention is human.

The compounds of formula I may be prepared from indoles of formula II as illustrated in Scheme 1 below where A, D, R, $R^1$, and Ar are as defined above and Pg is an amino protecting group.

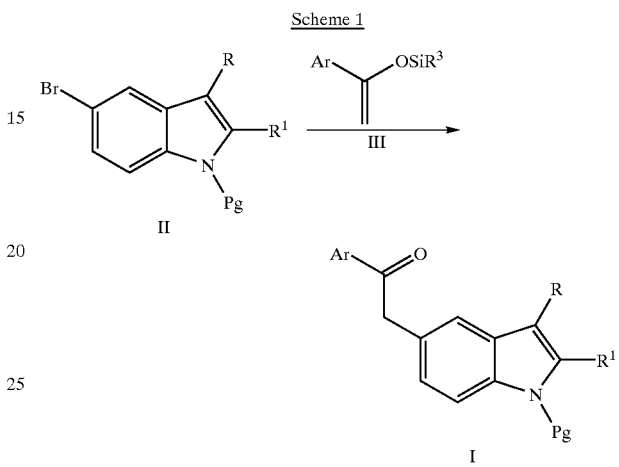

Scheme 1

Compounds of formula I may be prepared by various arylation methods. One such method is the arylation of silyl enol ethers of methyl ketones with aryl bromides. For a review of this method, see, e.g., JACS, 104:6831–6833, 1982. Such an arylation may be performed by dissolving or suspending a silyl enol ether of formula III, an aryl bromide, of formula II, a catalytic amount of palladium (II), and trialkyltin fluoride. Typical reaction temperatures range from ambient to the reflux temperature of the mixture. Preferably, the reaction is performed at the reflux temperature of the mixture. Typical reaction times range from 1 to about 48 hours but, generally, the reaction is substantially complete after about 5 hours.

Generally, the silyl enol ether is employed in a molar excess relative to the aryl bromide. Such excesses typically range from bout 1.01 to about 1.6 equivalents. Suitable sources of palladium include, but are not limited to Pd($PPh_3$)$_4$, Pd$Cl_2$($PPh_3$)$_2$, Pd$Cl_2$($Ph_2CH_2CH_2PPh_2$), Pd$Cl_2$(P(o-$CH_3C_6H_4$)$_3$)$_2$, and the like. Generally, about 3 molar percent of palladium is employed.

The skilled artisan would appreciate the need to protect the nitrogen of a compound of formula II during the reaction. For a discussion of optional protecting group, see the definitions provided supra. While the employed protecting group may be removed after the arylation of the a silyl enol, the deprotection step may be performed as desired at any point in the process after arylation.

The compounds of formula VIII and IX, where R is moiety (a), may be prepared substantially as described in U.S. Pat. No. 5,708,008 ('008), the teachings of which are herein incorporated by reference. These syntheses are illustrated below in Scheme 2 where $R^2$, and Ar are as defined above.

Scheme 2

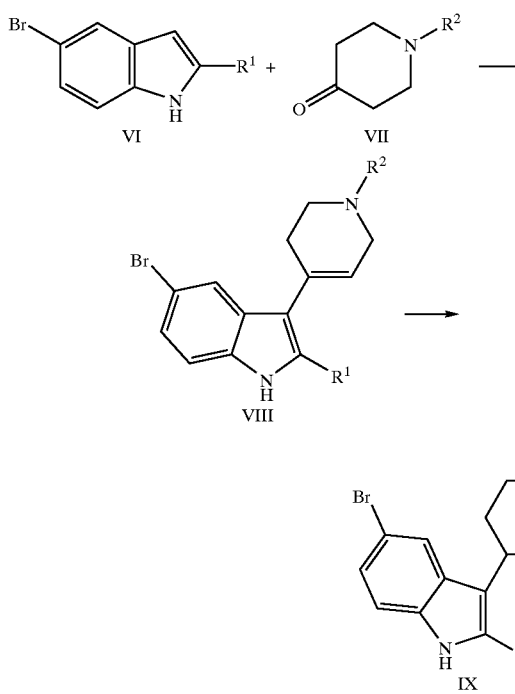

A compound of formula VI may be condensed with a compound of formula VII in the presence of a suitable base to give the corresponding compound of formula VIII. The reaction may be performed by adding the respective compounds of formula VI and VII to a mixture of an appropriate base (typically sodium or potassium hydroxide) in a lower alkanol, typically methanol or ethanol. About 1 to about 5 equivalents of a compound of formula VII, relative to the compound of formula VI are generally employed. A range of about 1.3 to 2.3 equivalents is preferred. The reaction is typically performed for about 0.25 to 24 hours.

If desired, compounds of formula VIII may be hydrogenated over a precious metal catalyst to give the corresponding compounds of formula IX. A catalyst such as sulfided platinum on carbon, platinum oxide, or a mixed catalyst system of sulfided platinum on carbon with platinum oxide may be used to prevent hydrogenolysis of that bromo substituent during the reduction. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20 p.s.i. to 80 p.s.i., preferably from 50 p.s.i. to 60 p.s.i., at 0° C. to 60° C., preferably at ambient temperature to 40° C., for 1 hour to 3 days. Additional charges of hydrogen may be required to drive the reaction to completion depending on the specific substrate.

Compounds of formula VIII and IX, prepared as described above may be utilized as in Scheme 1.

The compounds of formula VI may be prepared by methods well known to one of ordinary skill in the art, such as that generally described in U.S. Pat. No. 4,443,451, the teachings of which are hereby incorporated by reference. While these indoles are generally commercially available, their preparations are also described in Robinson, *The Fischer Indole Synthesis*, Wiley, N.Y., 1983; Hamel, et al., *Journal of Organic Chemistry*, 59:6372, 1994; and Russell, et al., *Organic Preparations and Procedures International*, 17:391, 1985.

The compounds of formula XI and XII, where R is moiety (c), may be prepared substantially as described in U.S. Pat. No. 5,708,008 ('008), the teachings of which are herein incorporated by reference. These syntheses are illustrated below in Scheme 3 where $R^2$, $R^3$, $R^4$ and Ar are as defined above.

Scheme 3

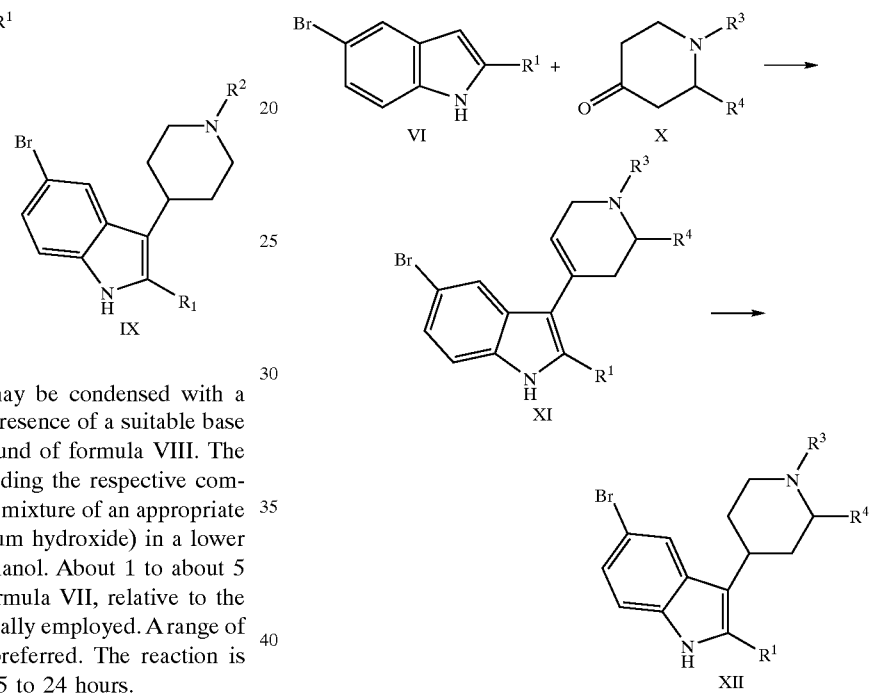

A compound of formula VI may be condensed with a compound of formula X in the presence of a suitable base to give the corresponding compound of formula XI. The reaction may be performed by adding the respective compounds of formula VI and X to a mixture of an appropriate base (typically sodium or potassium hydroxide) in a lower alkanol, typically methanol or ethanol. About 1 to about 5 equivalents of a compound of formula X, relative to the compound of formula VI are generally employed. A range of about1.3 to 2.3 equivalents is preferred. The reaction is typically performed for about 0.25 to 24 hours.

If desired, compounds of formula XI may be hydrogenated over a precious metal catalyst to give the corresponding compounds of formula XII. A catalyst such as sulfided platinum on carbon, platinum oxide, or a mixed catalyst system of sulfided platinum on carbon with platinum oxide may be used to prevent hydrogenolysis of that bromo substituent during the reduction. The hydrogenation solvent may consist of a lower alkanol, such as methanol or ethanol, tetrahydrofuran, or a mixed solvent system of tetrahydrofu ran and ethyl acetate. The hydrogenation may be performed at an initial hydrogen pressure of 20 p.s.i. to 80 p.s.i., preferably from 50 p.s.i. to 60 p.s.i., at 0° C. to 60° C., preferably at ambient temperature to 40° C., for 1 hour to 3 days. Additional charges of hydrogen may be required to drive the reaction to completion depending on the specific substrate.

Compounds of formula XI and XII, prepared as described above may be utilized as in Scheme 1.

Compounds of formula VIII may be prepared from methylvinyl ketone and an appropriate amino-dialkylacetal or cyclic acetal according to the procedures found in *Tet. Let.*, 24:3281, 1983, and *J.C.S. Perk. I*, 447, 1986. These acetals are generally commercially available or can be synthesized by well known methods in the art from their corresponding commercially available 4-substituted butanals or 5-substituted pentanals. This chemistry is illustrated in Scheme 4, $R^7$ and $R^8$ are $C_1$–$C_4$ alkyl or $R^7$ and $R^8$ taken together with the oxygen atoms, to which they are attached, form a 5 or 6 membered cyclic acetal, and n is 0, 1, or 2.

Scheme 4

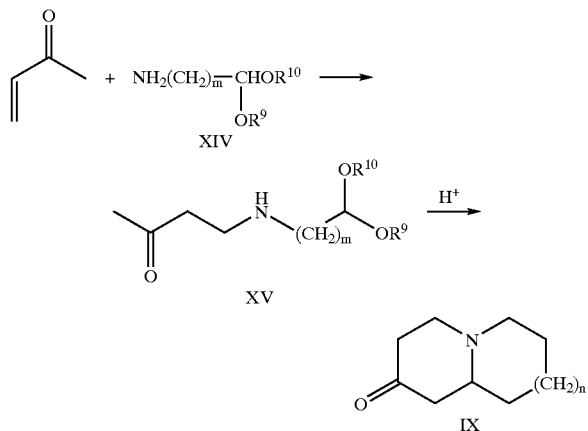

Compounds of formula IX may be prepared by acid treatment of the addition product of methyl vinyl ketone and a compound of formula XIV. A diethylacetal of formula XIV is a preferred starting material for this reaction ($R^9$ and $R^{10}$ are ethyl). The reaction may be performed by first dissolving an appropriate aminoacetal of formula XIV in an suitable solvent, typically diethyl ether at 0° C., and then adding approximately 1.7 equivalents of methyl vinyl ketone. Typically the reaction is allowed to stir at 0° C. for approximately 2 hours before acidification by addition of, or extraction with, aqueous hydrochloric acid. Typically, the organic layer is removed before heating the aqueous layer to approximately 100° C. for 1 hour. The resulting 7-octahydroindolizinone, 2-octahydro-2H-quinolizinone, or 4-(1-azabicyclo[5.4.0]undecan)ones of formula IX may be isolated from the reaction mixture by adjusting the pH of the solution to alkaline and extracting with a water immiscible solvent such as ethyl acetate or dichloromethane.

Compounds of formula IX prepared as described in Scheme 4 are racemic and, if used as described in Schemes 3, will produce racemic compounds of the invention. Compounds of the invention that are optically enhanced in one enantiomer may be obtained by resolving the compounds of formula IX before use of these compounds as described in Scheme 3. Methods of resolving enantiomeric compounds of this type are well known in the art. For example, resolution can be achieved by use of chiral chromatography. Furthermore, racemic compounds of formula IX may be converted to their corresponding diastereomeric mixture of salts by reaction with a chiral acid such as (+) or (–) tartaric acid. The diastereomers may then be separated and purified by recrystallization. Once separated, the salts may each be converted back to the chiral free base compounds of formula IX by reacting the salts with an aqueous base, such as sodium hydroxide, then extracting the mixture with a common organic solvent. The optical purity in resolved compounds of formula IX is maintained while undergoing the chemistry described in this application to afford optically pure compounds of the invention. As an alternative, when advantageous, the resolution techniques just discussed may be performed at any convenient point in the syntheses described in Schemes 3.

Compounds of formula VI, VII, and XIV are known in the art and, to the extent not commercially available, are readily synthesized by standard procedures commonly employed in the art such as those described herein.

The optimal time for performing the reactions of Schemes 1–4 may be determined by monitoring the progress of the reaction via conventional chromatographic techniques, e.g., thin layer chromatography and high performance liquid chromatography. Furthermore, it is usually preferred to conduct the reactions of Scheme 1–4 under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The intermediate compounds of this invention are preferably purified before their use in subsequent reactions. The intermediates and final products may be purified when, if in the course of their formation, they crystallize out of the reaction solution. In such a situation, the precipitate may be collected by filtration and washed with an appropriate solvent. Certain impurities may be removed from the organic reaction mixture by aqueous acidic or basic extraction followed by removal of the solvent by extraction, evaporation, or decantation. The intermediates and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention.

Preparation 1

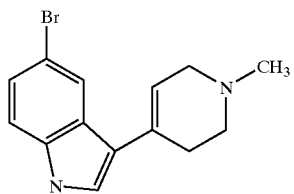

5-Bromo-3-(1-Methyl-1,2,3,6-Tetrahydropyridin-4-yl)-1H-Indole

To a solution of 56.11 gm (306 mmol) potassium hydroxide in 300 mL methanol was added 38 mL (306 mMol) 1-methyl-4-piperidone followed by 30.0 gm (153 mMol) 5-bromo-1H-indole. The reaction mixture was stirred at the reflux temperature of the mixture for 18 hours. The reaction mixture was then cooled to ambient and diluted with 1.5 L water. The resultant white solid was filtered, washed sequentially with water and diethyl ether, and then dried under vacuum to give 44.6 gm of the title compound. (100%).

Preparation 2

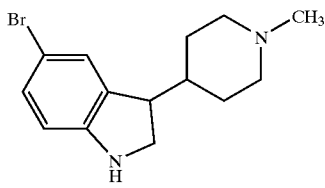

5-Bromo-3-(1-Methylpiperidin-4-yl)Indole

To a solution of 5-bromo-3-(a-methyl-1,2,3,6-tetrahydro-4-pyridinyl)-1H-indole (44.6 g, 153 mmol) in 1.95 L tetrahydrofuran was added 9.0 gm platinum oxide. The reaction mixture was hydrogenated with an initial hydrogen pressure of 60 p.s.i. at ambient temperature for 24 hours. The reaction mixture was filtered and the filtrate concentrated under reduced pressure. The residue was recrystallized from acetonitrile to give 32.6 gm (73.7%) of the title compound as a white solid. MS (m/e): 293(M+). EA calculated for $C_{14}H_{17}N_2Br$: C, 57.32; H, 5.96; N, 9.69. Found: C, 57.35; H, 5.84; N, 9.55.

Preparation 3

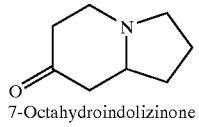

7-Octahydroindolizinone

Methylvinyl ketone (18.0 g, 256 mmol) was added dropwise to a solution of the 4,4-diethoxybutylamine (24.8 g, 154 mmol) in diethyl ether at 0° C. and stirred for one hour. The reaction was allowed to warm to room temperature and stir for 2 hours. The reaction was poured into 350 ml of 2N hydrochloric acid and the layers were separated. The aqueous layer was heated on a steam bath for 1 hour and then allowed to stir at 40° C. for 18 hours. The reaction was made basic with a sodium hydroxide solution and then extracted with methylene chloride. The extracts were dried over sodium sulfate and concentrated to give 20 g of an orange oil. This oil was distilled in vacuo at 74–84° C./5 mmHg to give 6168 g of racemic product. (31%).

MS(FD) (m/e): 139. $^1$H-NMR.

Preparation 4

Resolution of Racemic 7-Octahydroindolizinone

Step 1: Preparation of the (+)-Ditoluoyl Tartaric Acid Salts of 7-Octahydroindolizinone The (+)-ditoluoyl tartaric acid monohydrate (19.7 g, 49 mmol) was dissolved in 100 ml of warm methanol and the racemic 7-octahydroindolizinone (6.86 g, 49 mmol) in 25 ml of methanol was added. The reaction was thoroughly mixed and allowed to stand at room temperature for about 18 hours. No precipitate had formed so the material was concentrated by boiling and ethyl acetate was added. At the point where solid began to form, the reaction was cooled to room temperature and a precipitate formed. This material was collected by filtration. The filter cake was recrystallized twice from methanol/acetonitrile to give 7.87 g a product which was approximately a 2:1 mixture of diastereomers. (31%).

EA calculated for $C_8H_{13}NO \cdot C_{20}H_{18}O_8$:

Theory: C, 63.99; H, 5.95; N, 2.67.

Found: C, 63.92; H, 5.98; N, 2.55.

Step 2: Preparation of the Chiral 7-Octahydroindolizinone Free Amine

The (+)-ditoluoyl tartaric acid salt of 7-octahydroindolizinone (7.42 g, 14 mmol) from step 1 was suspended in methylene chloride/0.5 M sodium hydroxide solution and stirred until no solid was visible. The layers were separated and the aqueous layer extracted with methylene chloride. The combined organic extracts were dried over sodium sulfate and concentrated to give 2.00 g of a light yellow oil. (100%). MS(FD) (m/e): 139.

Example 1

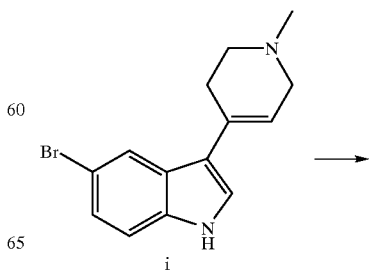

i

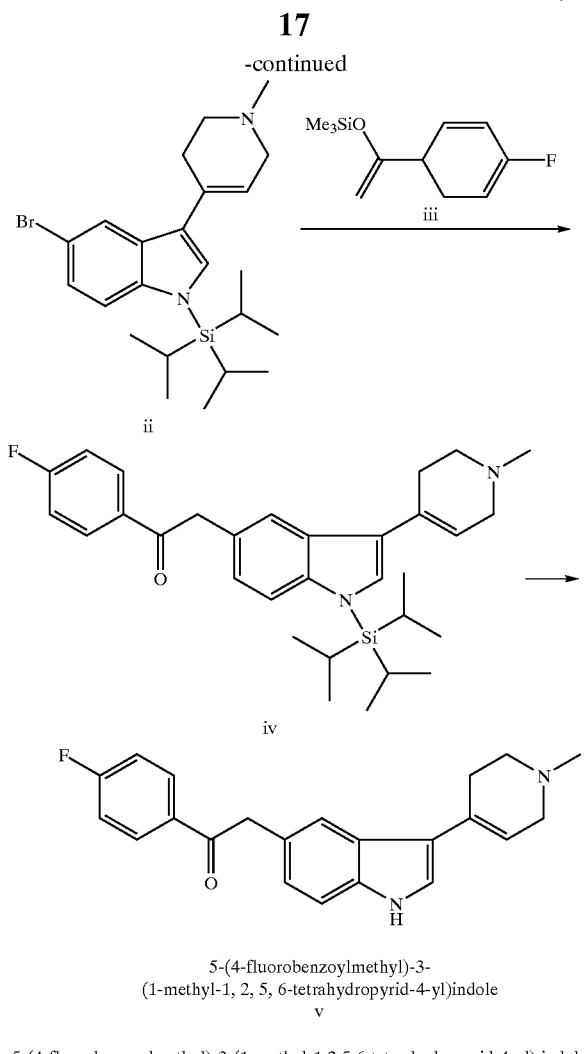

5-(4-fluorobenzoylmethyl)-3-
(1-methyl-1, 2, 5, 6-tetrahydropyrid-4-yl)indole
v 5-(4-fluorobenzoylmethyl)-3-(1-methyl-1,2,5,6-tetra-hydropyrid-4-yl) indole Potassium hydride (4.79 g, 20%, 23.9 mmol) was suspended in tetrahydrofuran (60 mL). After the mixture was cooled to 0° C., a solution of 5-bromo-3-(1-methyl-1,2,3,6-tetrahydropyridin-4-yl)indole (3.48 g, 11.9 mmol) in 20 mL of tetrahydrofuran was slowly introduced. The mixture was stirred at 0° C. for 1 h before TipsOTf (4.79 g, 15.6 mmol) was added. The resulting mixture was stirred at room temperature for 3 h. Water was added dropwise to quench the excess KH. The product was extracted with ethyl acetate (50 mL×3). The combined organic layers were washed with water, dried, filtered, and concentrated. The residue was purified by flash chromatography using 6% MeOH, 0.5% NH$_4$OH in CH$_2$Cl$_2$ to give product ii (3.71 g, 8.3 mmol) in 69% yield.

To a solution of ii (1.04 g, 2.3 mmol) in 8 mL of toluene, were added in order compound iii (0.49 g, 2.3 mmol), n-Bu$_3$SnF (0.72 g, 2.3 mmol), PdCl$_2$ (42 mg, 0.24 mmol) and tri-O-tolyphosphine (146 mg, 0.48 mmol). The mixture was then heated to reflux for 5 h. After cooled, the mixture was filtered to remove the solid starting materials and by-products. The filtrate was evaporated to a residue that was purified by flash chromatography using a 5:4:1 mixture of hexanes, CH$_2$Cl$_2$, and ethyl acetate to give product iv (495 mg, 0.98 mmol) in 43% yield.

To a stirred solution of iv (296 mg, 0.58 mmol) in 8 mL of THF was added a solution of n-Bu$_4$NF (1M, 0.60 mL, 0.60 mmol) in THF. The mixture was stirred at room temperature for 30 min. Water (30 mL) and CH$_2$Cl$_2$ (60 mL) were added. The organic layer was separated, washed with water, dried, filtered, and concentrated. The residue was purified by flash chromatography using 10% MeOH, 0.5% NH$_4$OH in CH$_2$Cl$_2$ to provide product 5-(4-fluorobenzoylmethyl)-3-(1-methyl-1,2,5,6-tetahydropyrid-4-yl)indole(87 mg, 0.25 mmol) in 43% yield.

Oxalate salt of 5-(4-fluorobenzoylmethyl)-3-(1-methyl-1, 2,5,6-tetrahydropyrid-4-yl)indole was prepared.

MS 349(M+1); mp 197–200° C.

The compounds of this invention are useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. For further instruction on the nexus between activation of the 5-HT$_{1F}$ and migraine, see the previously incorporated by reference U.S. Pat. No. 5,708,008.

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90:408–412, 1993.

Membrane Preparation: Membranes were prepared from transfected Ltk− cells (transfected with the human 5HT$_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford. *Anal. Biochem.*, 72:248–254, 1976.

Radioligand Binding: [$^3$H-5-HT] binding was performed using slight modifications of the 5-HT$_{1D}$ assay conditions reported by Herrick-Davis and Titeler (*J. Neurochem.*, 50:1624–1631, 1988) with the omission of masking ligands. Radioligand binding studies were achieved at 37° C. in a total volume of 250 mL of buffer (50 mM Tris, 10 mM MgCl$_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC50 values were converted to $K_i$ values using the Cheng-Prusoff equation. *Biochem. Pharmacol.*, 22:3099–3108, 1973. All experiments were performed in triplicate. Representative compounds of this invention were found to have affinity for the 5-HT$_{1F}$ receptor as measured by the procedure described above.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. N. Adham, et al., supra,; R. L. Weinshank, et al., *Proceedings of the National Academy of Sciences (USA)*, 89:3630–3634, 1992; and the references cited therein.

Measurement of cAMP formation: Human 5HT$_{1F}$ receptor transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% $CO_2$. Drug dose-effect curves were then conducted by adding 6 different final concentrations of drug, followed immediately by the addition of forskolin (10 mM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention shown to have affinity for the 5-HT$_{1F}$ receptor were tested and found to be agonists at the 5-HT$_{1F}$ receptor in the cAMP assay.

The type of formulation employed for the administration of the compounds employed in the methods of the present invention may be dictated by the particular compounds employed, the type of pharmacokinetic profile desired from the route of administration and the compound(s), and the state of the patient.

Formulations amenable to oral or injectable administration are prepared in a manner well known in the pharmaceutical art and comprise at least one active compound. See, e.g., *Remington's Pharmaceutical Sciences*, (16th ed., 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a compound of formula I.

Formulation Example 1
Hard Gelatin Capsules

| Ingredient | Quantity (mg/capsule) |
| --- | --- |
| Active ingredient | 30.0 |
| Starch | 305.0 |
| Magnesium stearate | 5.0 |

The above ingredients are mixed and filled into hard gelatin capsules in 340 mg quantities.

Formulation Example 2
Tablet

| Ingredient | Quantity (mg/tablet) |
|---|---|
| 5-(2-pyrazol-4-ylethylcarbonyl)-3-(1-methylpiperidin-4-yl)-indole | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3
Dry Powder Inhaler

| Ingredient | Weight % |
|---|---|
| 5-(3-isopropylbenzoylmethyl)-3-(1-methyl-1,2,3,6-tetrahydro-pyrid-4-yl)indole | 5 |
| Lactose | 95 |

The active ingredient is mixed with the lactose and the mixture is added to a dry powder inhaling appliance.

Formulation Example 4
Tablet

| Ingredient | Quantity (mg/tablet) |
|---|---|
| 5-(2-bromobenzoylmethyl)-3-(1-methylpiperidin-4-yl)indole | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5
Capsules

| Ingredient | Quantity (mg/capsule) |
|---|---|
| 5-(2-fluorobenzoylmethyl)-3-(indolizidin-6-yl)indole | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6
Suppositories

| Ingredient | Amount |
|---|---|
| 5-(3-chlorobenzoylmethyl)-3-[(1-methylpyrrolidin-2-yl)methyl]indole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7
Suspensions

| Ingredient | Amount |
|---|---|
| 5-(2,3-diiodobenzoylmethyl)-3-(1-methyl-1,2,3,6-tetrahydro-pyrid-4-yl)indole | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8
Capsules

| Ingredient | Quantity (mg/capsule) |
| --- | --- |
| 5-(2,4-diaminobenzoylmethyl)-3-[(1-methylpyrrolidin-2-yl)methyl]indole | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9
Intravenous Formulation

| Ingredient | Quantity |
| --- | --- |
| 5-(2-methylbenzoylmethyl)-3-(indolizidin-6-yl)indole | 250.0 mg |
| Isotonic saline | 1000 ml |

Formulation Example 10
Topical Formulation

| Ingredient | Quantity |
| --- | --- |
| 5-(2,4-dichlorobenzoylmethyl)-3-(1-methyl-1,2,3,6-tetrahydropyrid-4-yl)indole | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11
Sublingual or Buccal Tablets

| Ingredient | Quantity (mg/tablet) |
| --- | --- |
| 5-(2-thien-3-ylethylcarbonyl)-3-(1-methylpiperidin-4-yl)-indole | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of formula I:

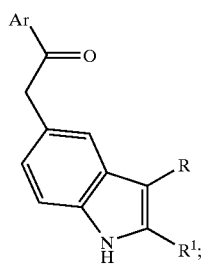

or a pharmaceutical acid addition salt thereof, where;

R is (a) 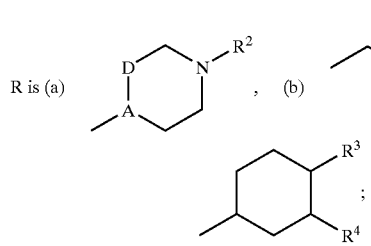, (b) 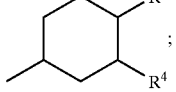, or (c)

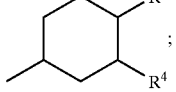

A—D is CH—CH$_2$ or C=CH;
R$^1$ is hydrogen or C$_1$–C$_4$ alkyl;
R$^2$ is hydrogen, C$_1$–C$_6$ alkyl, C$_2$–C$_6$ alkenyl, C$_2$–C$_6$ alkynyl, Ar, or Ar—(C$_1$–C$_4$ alkyl);
R$^3$ and R$^4$ combine, together with the 6 membered ring to which they are attached, to form a 6:5, 6:6, or 6:7 fused bicyclic ring; and
Ar is an optionally substituted phenyl or optionally substituted heteroaryl, where "substituted phenyl" is taken to mean that the phenyl moiety is substituted with one substituent selected from the group consisting of halo, nitro, cyano, amino, trifluoromethyl, trifluoromethoxy, phenyl, benzoyl, C$_1$–C$_6$ alkyl, C$_1$–C$_6$ alkoxy, (C$_1$–C$_4$ alkyl)S(O)$_n$, where n is 0, 1, or 2, (C$_1$–C$_4$ alkyl)$_2$ amino, C$_1$–C$_4$ acyl, or two to three substituents independently selected from the group consisting of halo, nitro, trifluoromethyl, C$_1$–C$_4$ alkyl, or C$_1$–C$_4$ alkoxy, and where "substituted heteroaryl" is taken to mean that the heteroaryl moiety is substituted with substituents selected from the group consisting of halo, nitro, cyano, amino, trifluoromethyl, trifluoromethoxy, phenyl, benzoyl, C$_1$–C$_6$ alkyl, C$_1$–C$_6$ alkoxy, C$_1$–C$_4$ acyl, (C$_1$–C$_4$)$_n$ amino where n is 0, 1, or 2.

2. The compound of claim 1 where A—D is CH—CH$_2$.
3. The compound of claim 1 where R is moiety (a).
4. The compound of claim 3 where Ar is an optionally substituted phenyl.
5. The compound of claim 4 where Ar is 4-fluorophenyl.
6. The compound of claim 1 where R is moiety (b).
7. The compound of claim 6 where Ar is an optionally substituted phenyl.
8. The compound of claim 7 where Ar is 4-fluorophenyl.
9. The compound of claim 1 where R is moiety (c).
10. The compound of claim 9 where Ar is an optionally substituted phenyl.
11. The compound of claim 10 where Ar is 4-fluorophenyl.
12. A pharmaceutical formulation comprising a compound of formula I:

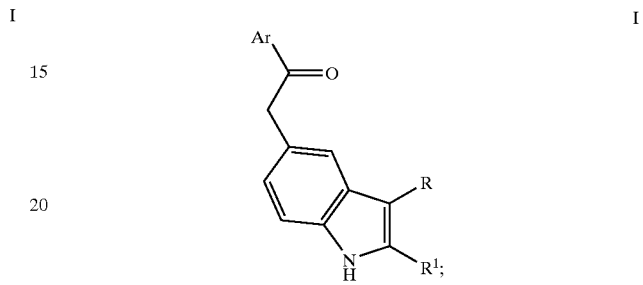

where;

R is (a) 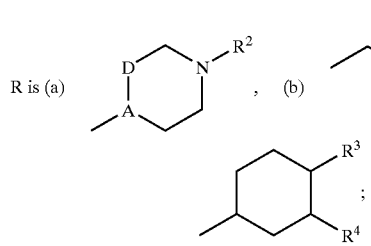, (b) 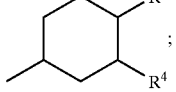, or (c)

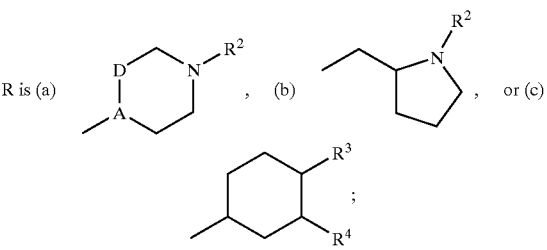

A—D is CH—CH$_2$ or C=CH;
R$^1$ is hydrogen or C$_1$–C$_4$ alkyl;
R$^2$ is hydrogen, C$_1$–C$_6$ alkyl, C$_2$–C$_6$ alkenyl, C$_2$–C$_6$ alkynyl, Ar, or Ar—(C$_1$–C$_4$ alkyl);
R$^3$ and R$^4$ combine, together with the 6 membered ring to which they are attached, to form a 6:5, 6:6, or 6:7 fused bicyclic ring; and
Ar is an optionally substituted phenyl or optionally substituted heteroaryl, where "substituted phenyl" is taken to mean that the phenyl moiety is substituted with one substituent selected from the group consisting of halo, nitro, cyano, amino, trifluoromethyl, trifluoromethoxy, phenyl, benzoyl, C$_1$–C$_6$ alkyl, C$_1$–C$_6$ alkoxy, (C$_1$–C$_4$ alkyl)S(O)$_n$, where n is 0, 1, or 2, (C$_1$–C$_4$ alkyl)$_2$ amino, C$_1$–C$_4$ acyl, or two to three substituents independently selected from the group consisting of halo, nitro, trifluoromethyl, C$_1$–C$_4$ alkyl, or C$_1$–C$_4$ alkoxy, and where "substituted heteroaryl" is taken to mean that the heteroaryl moiety is substituted with substituents selected from the group consisting of halo, nitro, cyano, amino, trifluoromethyl, trifluoromethoxy, phenyl, benzoyl, C$_1$–C$_6$ alkyl, C$_1$–C$_6$ alkoxy, C$_1$–C$_4$ acyl, and (C$_1$–C$_4$)$_n$ amino where n is 0, 1, or 2;
or a pharmaceutical acid addition salt thereof, and a pharmaceutically acceptable carrier, diluent, or excipient.

13. The pharmaceutical formulation of claim 12 where R is moiety (a).
14. The pharmaceutical formulation of claim 13 where Ar is 4-fluorophenyl.

15. The pharmaceutical formulation of claim 12 where R is moiety (b).

16. The pharmaceutical formulation of claim 15 where Ar is 4-fluorophenyl.

17. The pharmaceutical formulation of claim 12 where R is moiety (c).

18. The pharmaceutical formulation of claim 17 where Ar is 4-fluorophenyl.

19. A method for activating 5-HT1F receptors in a mammal comprising administering to a mammal in need of such activation an effective amount of a compound of formula I:

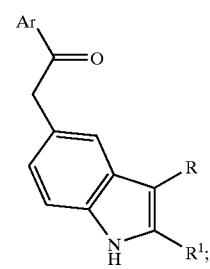

where;

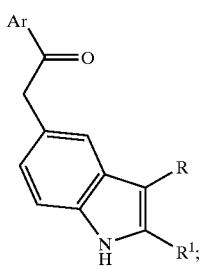

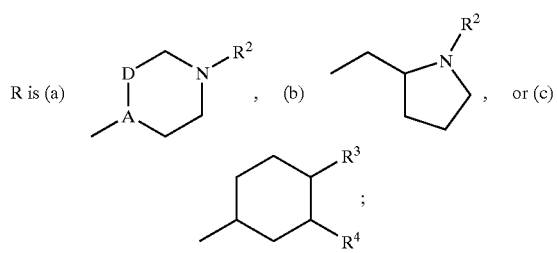

A—D is CH—CH$_2$ or C=CH;

R$^1$ is hydrogen or C$_1$–C$_4$ alkyl;

R$^2$ is hydrogen, C$_1$–C$_6$ alkyl, C$_2$–C$_6$ alkenyl, C$_2$–C$_6$ alkynyl, Ar, or Ar—(C$_1$–C$_4$ alkyl);

R$^3$ and R$^4$ combine, together with the 6 membered ring to which they are attached, to form a 6:5, 6:6, or 6:7 fused bicyclic ring; and Ar is an optionally substituted phenyl or optionally substituted heteroaryl, where "substituted phenyl" is taken to mean that the phenyl moiety is substituted with one substituent selected from the group consisting of halo, nitro, cyano, amino, trifluoromethyl, trifluoromethoxy, phenyl, benzoyl, C$_1$–C$_6$ alkyl, C$_1$–C$_6$ alkoxy, (C$_1$–C$_4$ alkyl)S(O)$_n$, where n is 0, 1, or 2, (C$_1$–C$_4$ alkyl)$_2$ amino, C$_1$–C$_4$ acyl, or two to three substituents independently selected from the group consisting of halo, nitro, trifluoromethyl, C$_1$–C$_4$ alkyl, or C$_1$–C$_4$ alkoxy, and where "substituted heteroaryl" is taken to mean that the heteroaryl moiety is substituted with substituents selected from the group consisting of halo, nitro, cyano, amino, trifluoromethyl, trifluoromethoxy, phenyl, benzoyl, C$_1$–C$_6$ alkyl, C$_1$–C$_6$ alkoxy, C$_1$–C$_4$ acyl, and (C$_1$–C$_4$)$_n$ amino where n is 0, 1, or 2;

or a pharmaceutical acid addition salt thereof.

20. The method according to claim 19 where the mammal is a human.

21. A method for inhibiting neuronal protein extravasation in a mammal comprising administering to a mammal in need of such inhibition an effective amount of a compound of formula I:

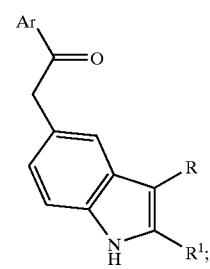

where;

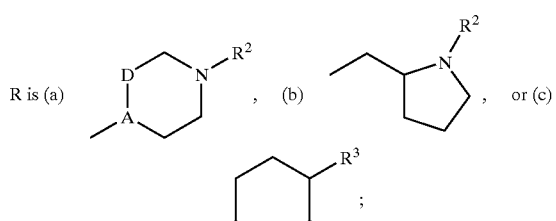

A—D is CH—CH$_2$ or C=CH;

R$^1$ is hydrogen or C$_1$–C$_4$ alkyl;

R$^2$ is hydrogen, C$_1$–C$_6$ alkyl, C$_2$–C$_6$ alkenyl, C$_2$–C$_6$ alkynyl, Ar, or Ar—(C$_1$–C$_4$ alkyl);

R$^3$ and R$^4$ combine, together with the 6 membered ring to which they are attached, to form a 6:5, 6:6, or 6:7 fused bicyclic ring; and Ar is an optionally substituted phenyl or optionally substituted heteroaryl, where "substituted phenyl" is taken to mean that the phenyl moiety is substituted with one substituent selected from the group consisting of halo, nitro, cyano, amino, trifluoromethyl, trifluoromethoxy, phenyl, benzoyl, C$_1$–C$_6$ alkyl, C$_1$–C$_6$ alkoxy, (C$_1$–C$_4$ alkyl)S(O)$_n$, where n is 0, 1, or 2, (C$_1$–C$_4$ alkyl)$_2$ amino, C$_1$–C$_4$ acyl, or two to three substituents independently selected from the group consisting of halo, nitro, trifluoromethyl, C$_1$–C$_4$ alkyl, or C$_1$–C$_4$ alkoxy, and where "substituted heteroaryl" is taken to mean that the heteroaryl moiety is substituted with substituents selected from the group consisting of halo, nitro, cyano, amino, trifluoromethyl, trifluoromethoxy, phenyl, benzoyl, C$_1$–C$_6$ alkyl, C$_1$–C$_6$ alkoxy, C$_1$–C$_4$ acyl, and (C$_1$–C$_4$)$_n$ amino where n is 0, 1, or 2; or a pharmaceutical acid addition salt thereof.

22. The method according to claim 21 where the mammal is a human.

23. A method for treating migraine in a mammal comprising administering to a mammal in need of such treatment an effective amount of a compound of formula I:

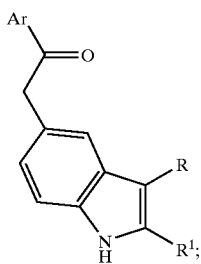

where;

R is (a) 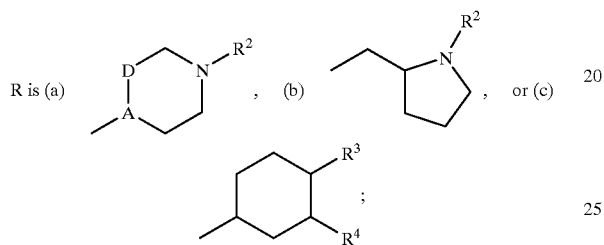

A—D is CH—CH$_2$ or C=CH;

$R^1$ is hydrogen or $C_1$–$C_4$ alkyl;

$R^2$ is hydrogen, $C_1$–$C_6$ alkyl, $C_2$–$C_6$ alkenyl, $C_2$–$C_6$ alkynyl, Ar, or Ar—($C_1$–$C_4$ alkyl);

$R^3$ and $R^4$ combine, together with the 6 membered ring to which they are attached, to form a 6:5, 6:6, or 6:7 fused bicyclic ring; and Ar is an optionally substituted phenyl or optionally substituted heteroaryl, were "substituted phenyl" is taken to mean that the phenyl moiety is substituted with one substituent selected from the group consisting of halo, nitro, cyano, amino, trifluoromethyl, trifluoromethoxy, phenyl, benzoyl, $C_1$–$C_6$ alkyl, $C_1$–$C_6$ alkoxy, ($C_1$–$C_4$ alkyl)S(O)$_n$, where n is, 0, 1, or 2, ($C_1$–$C_4$ alkyl)$_2$ amino, $C_1$–$C_4$ acyl, or two to three substituents independently selected from the group consisting of halo, nitro, trifluoromethyl, $C_1$–$C_4$ alkyl, or $C_1$–$C_4$ alkoxy, and where "substituted heteroaryl" is taken to mean that the heteroaryl moiety is substituted with substituents selected from the group consist of halo, nitro, cyano, amino, trifluoromethyl, trifluoromethoxy, phenyl, benzoyl, $C_1$–$C_6$ alkyl, $C_1$–$C_6$ alkoxy, $C_1$–$C_4$ acyl, and ($C_1$–$C_4$)$_n$ amino where n is 0, 1, or 2; or a pharmaceutical acid addition salt thereof.

24. The method according to claim 23 where the mammal is a human.

* * * * *